Aug 21, 1951 J. DE VINK Plant Pat. 1,032
ROSE PLANT
Filed June 2, 1950
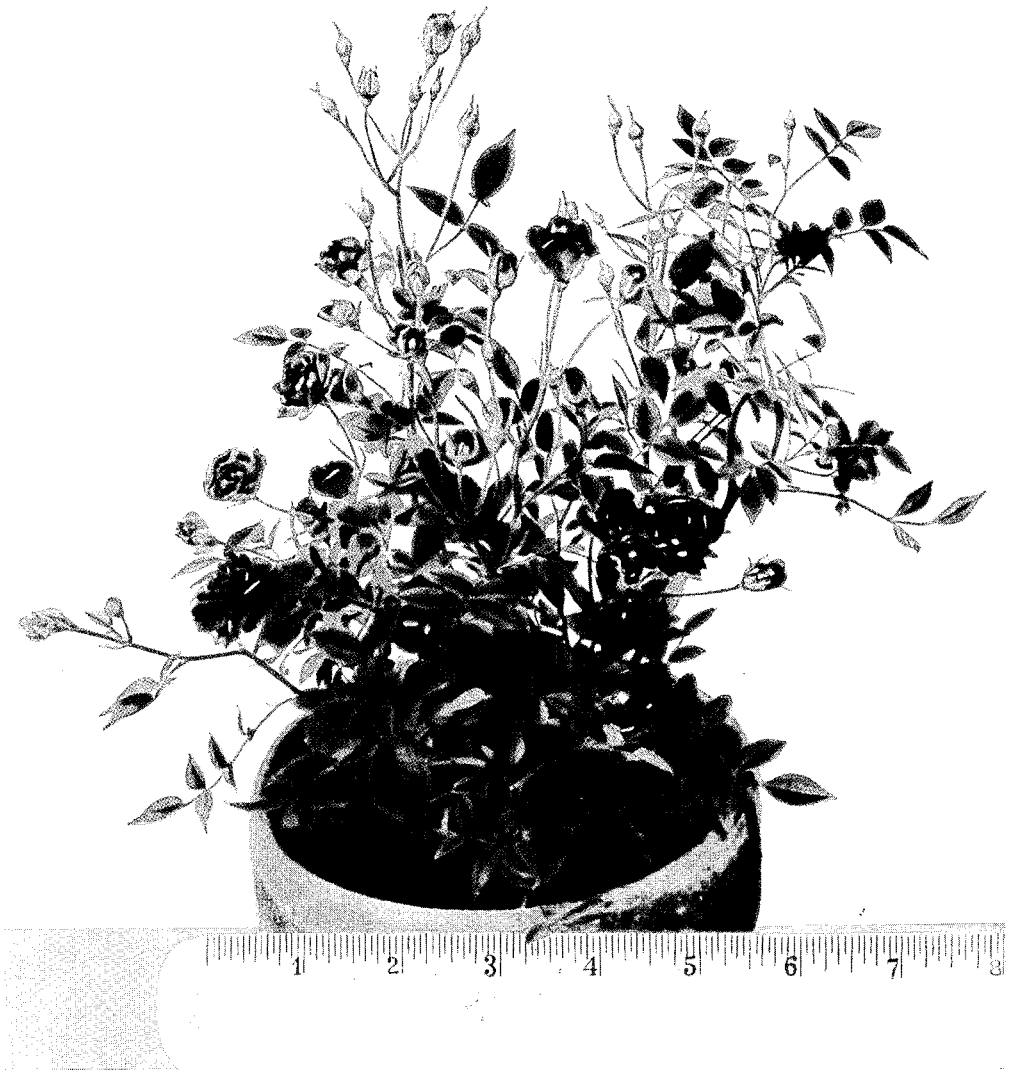
Inventor.
John de Vink
By: Robert Cook
Attorney.

Patented Aug. 21, 1951

Plant Pat. 1,032

UNITED STATES PATENT OFFICE 1,032

ROSE PLANT

John de Vink, Boskoop, Netherlands, assignor to The Conard-Pyle Company, West Grove, Pa., a corporation of Pennsylvania Application June 2, 1950, Serial No. 165,693

1 Claim. (Cl. 47—61)

The present invention relates to a new and distinct variety of rose plant of the miniature rose class, originated by crossing the unpatented variety "Ellen Poulsen" × "Tom Thumb" (Plant Patent No. 169).

This new rose variety is dominantly characterized by its superiority in color, and long-lasting retention of its deep crimson color, to any other red miniature rose variety.

In addition to the foregoing characteristics, this new variety is distinguished from its parents, as well as from other miniature rose varieties, by the following important and desirable features:

(1) Unlike other red miniature roses, it is almost entirely free from an blemishes of bits of white at the base of its flower petals;

(2) Almost never are to be seen white coloration or yellow stamens that are so characteristic of other red varieties;

(3) Its flowers are very double, having from 45 to 60 petals, as compared with approximately 15 petals in the flowers of its parent "Tom Thumb," and about 25 petals in the flowers of the two well-known varieties "Red Elf" (unpatented) and "Midget" (Plant Patent No. 466); and (4) Even when fully open, the flowers of this new variety continue to be exceptionally distinctive and attractive.

Asexual reproduction of this new variety by budding at Boskoop, Holland, and by budding and own-rooting at West Grove, Pennsylvania, U. S. A., shows that the foregoing characteristics come true to form and are established and transmitted through succeeding propagations.

The accompanying drawing shows a potted specimen plant of the new variety, in comparison with an inch-marked scale, with the flowers and foliage of the plant depicted in different stages of development.

The following is a detailed description of the new variety, with color terminology in accordance with Ridgway's Color Standards and Nomenclature, except where general color terms of ordinary dictionary significance are used:

Type: Hardy; dwarf; greenhouse; outdoor; seedling; for cut flowers and garden decoration.
Class: Miniature.
Breeding: Seedlings.
*Seed parent.*—"Ellen Poulsen" (unpatented).
*Pollen parent.*—"Tom Thumb" (Plant Patent No. 169).
Propagation: Holds its distinguishing characteristics through succeeding propagations by cuttings and budding.

*Flower*

Locality where grown: West Grove, Pennsylvania.
Flowers borne: Several to stem; in irregular cluster; on strong, long stems.
Quantity of bloom: Free in greenhouse.
Continuity: Continuous.
Fragrance: Slight.
Bud:
*Peduncle.*—Long; medium heavy; erect; light green; entirely smooth.
*Before calyx breaks.*—Size—small. Form—medium ovoid; with foliaceous appendages on the surface of the bud; with entire foliaceous parts extending beyond the tip of the bud equal to one-fourth or more of its length.
*As calyx breaks.*—Color—Pomegranate Purple, Plate XII.
*As first petal opens.*—Size—medium. Form—medium length; cylindrical cup-shaped. Color—outside: Pomegranate Purple, Plate XII; inside: base white, veined with Pale Cendre Green, Plate VI: Pomegranate Purple, Plate XII, shading to dark velvety Carmine, Plate I, over most of petal surface.
*Opening.*—Opens up well, but is retarded from opening by cold weather.
Bloom:
*Size when fully open.*—Small; ¾ inch to 1 inch.
*Petalage.*—Very double; from 45 to 60 petals; arranged regularly.
*Form.*—Very full and cupped at first, becoming very flat; petals being at first loosely cupped inward with edges loosely curved outward; becoming later, at maturity, loosely rolled outward.
Petals: Medium thick; with inside velvety and outside satiny.
*Shape.*—Outer—obovate with apex coming to a small point. Intermediate—oval to obovate with apex coming to a small point. Inner—oval to obovate with apex coming to a small point.
*Color.*—Colors may be modified by being shaded with other colors.

This description of a newly opened flower was made from a rose grown in a greenhouse in the month of November, at West Grove, Pennsylvania:

*Color.*—Outer petal—outside surface: Pomegranate Purple, Plate XII; inside surface: Pomegranate Purple, Plate XII, shading to dark velvety Carmine, Plate I, over most of petal surface; white at base. Intermediate petal—outside surface: Pomegranate Purple, Plate XII; white at base; inside surface: dark velvety Carmine, Plate I; white at base. Inner petal—outside surface: Pomegranate Purple, Plate XII; white at base; inside surface: dark velvety Carmine, Plate I; white at base.

This description was made from a rose that was open for three days in a greenhouse in the month of November, at West Grove, Pennsylvania:

*Color.*—Outer petal—outside surface: Pomegranate Purple, Plate XII; white at base; inside surface: Dark Velvety Carmine, Plate I, shading almost to velvety Oxblood Red, Plate I; white at base. Inner petal—outside surface: Pomegranate Purple, Plate XII; white at base; inside surface: dark velvety Carmine, Plate I, shading almost to velvety Oxblood Red, Plate I; white at base.

*General color effect.*—Newly opened flower—dark velvety Carmine, Plate I, shading almost to Oxblood Red, Plate I, at center. Three days open—dark velvety Carmine, Plate I, shading to velvety Oxblood Red, Plate I.

*Behavior.*—Persist; fading purple; affected by hot weather by bluing slightly under extremes of heat.

*Flower longevity.* — On bush in greenhouse—10 to 11 days in November. Cut roses grown in greenhouse kept at living room temperatures—3 to 4 days in November.

*Reproductive organs*

Stamens: Medium number; most arranged regularly about pistils; partly mixed with petaloids.
Filaments: Most with anthers; medium length; white.
Anthers: All open at once; medium size; yellow; occasionally an anther fused with a petaloid.
Pollen: None found.
Pistils: Medium number.
Styles: Uneven; medium length; medium heavy; bunched.
Stigma: White.
Ovaries: All enclosed in calyx.
Hips: None found.
Sepals: Permanent; moderately short; spear-shaped.
Seeds: None found.

*Plant*

Foliage:

*Leaves.*—Usually compound of seven leaflets; normally abundant; medium size; moderately heavy.

*Leaflets.*—Shape—ovoid with apex acute; base round; margin simply serrate.

*Color.* — *Mature* — upper surface — Cedar Green, Plate VI; under surface—Light Elm Green, Plate XVII. *Young*—upper surface—Hellebore Green, Plate XVII; under surface—Light Hellebore Green, Plate XVII.

*Rachis.*—Medium heavy. Upper side—grooved. Under side—moderately thorny.

*Stipules.*—Medium length; medium white; with moderately short points; turning out at an angle of more than 45°.

*Disease.*—Resistant to mildew and moderately resistant to blackspot.

Growth:

*Habit.*—Bushy; upright; much branched.

*Growth.*—Free; average overall height 9 inches.

*Canes.*—Medium heavy.

*Main stems.*—Bright green. Thorns——several; long; hooked downward; with long oval base. Prickles and hairs—none.

*Branches.*—Bright green. Thorns—few; long; hooked downward; with medium length oval base. Prickles and hairs—none.

*New shoots.*—Bright green. Thorns—Very few; medium length; hooked downward; with medium length oval base. Prickles and hairs—none.

I claim:

A new and distinct variety of rose plant of the miniature rose class, characterized as to novelty by the deep crimson and long-lasting retention of the color of its flowers, by the relative freedom from blemishes of bits of white at the base of its flower petals, by the relative absence of white coloration and yellow stamens, by the very double form of its flowers, and by the persistence of the distinctive appearance of the flowers through the full-open stage, substantially as shown and described.

JOHN DE VINK.

No references cited.